US012605408B2

(12) United States Patent
Ovali et al.

(10) Patent No.: US 12,605,408 B2
(45) Date of Patent: Apr. 21, 2026

(54) METHOD FOR THE PRODUCTION OF A PRODUCT USED FOR IMMUNE MODULATION AND REGENERATION PURPOSES IN ALOPECIA AREATA, ANDROGENETIC ALOPECIA, SCAR, NEURODEGENERATIVE INFLAMMATORY DISEASES

(71) Applicants: Ercüment Ovali, Istanbul (TR); ACIBADEM MEHMET ALİ AYDINLAR ÜNİVERSİTESİ, Istanbul (TR); ACIBADEM LABMED SAĞLIK HİZMETLERİ ANONİM ŞİRKETİ, Istanbul (TR)

(72) Inventors: Ercüment Ovali, Istanbul (TR); Gamze Tümentemur, Istanbul (TR)

( * ) Notice: Subject to any disclaimer, the term of this patent is extended or adjusted under 35 U.S.C. 154(b) by 104 days.

(21) Appl. No.: 18/253,343

(22) PCT Filed: Jun. 24, 2022

(86) PCT No.: PCT/TR2022/050661
§ 371 (c)(1),
(2) Date: May 17, 2023

(87) PCT Pub. No.: WO2023/244189
PCT Pub. Date: Dec. 21, 2023

(65) Prior Publication Data
US 2024/0350555 A1      Oct. 24, 2024

(30) Foreign Application Priority Data
Jun. 15, 2022    (TR) ............................... 2022/009965

(51) Int. Cl.
*A61K 35/50*        (2015.01)
*A61K 9/00*        (2006.01)
(52) U.S. Cl.
CPC ............ *A61K 35/50* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 5,362,442 A | 11/1994 | Kent | |
| 9,161,954 B2 | 10/2015 | Tseng et al. | |
| 2008/0286378 A1* | 11/2008 | Behrens .................. | A61P 27/02 |
| | | | 424/528 |
| 2015/0025366 A1* | 1/2015 | Harrell .................... | A61M 1/60 |
| | | | 600/576 |

FOREIGN PATENT DOCUMENTS

| | | |
|---|---|---|
| CN | 107217028 A | 9/2017 |
| EP | 1780267 B1 | 1/2016 |
| EP | 3145490 B1 | 3/2018 |
| TR | 2019/14272 A1 | 9/2019 |
| WO | 2010107287 A2 | 9/2010 |

OTHER PUBLICATIONS

International Search Report and Written Opinion of the International Searching Authority for corresponding PCT/TR2022/050661 dated Feb. 22, 2023.

* cited by examiner

*Primary Examiner* — Susan Hoffman

(57) ABSTRACT

Disclosed is a production method of a product that is developed for treatment of hair loss, alopecia areata (pelade or ringworm), androgenetic alopecia (AGA), hair follicle nourishment, scalp nourishment and scar, scar tissue, eczema, acne treatments, for neurodegenerative, inflammatory diseases and for immune modulation purposes (regulation of the immunological response against inflammation of human tissues and fluids, for regeneration purposes). In particular, the disclosed is a method for the production of a chemical-free product with amniotic fluid content, which has been standardized by pooling and then freeze-dried and gamma irradiated (pooled/cocktail and gamma irradiated amnion-OTIA 1.0), that has been developed to be used in the treatment of ailments such as hair loss, alopecia areata (pelade), androgenetic alopecia (AGA), hair follicle nutrition, scalp nourishment, scar, scar tissue, eczema and acne.

7 Claims, No Drawings

METHOD FOR THE PRODUCTION OF A PRODUCT USED FOR IMMUNE MODULATION AND REGENERATION PURPOSES IN ALOPECIA AREATA, ANDROGENETIC ALOPECIA, SCAR, NEURODEGENERATIVE INFLAMMATORY DISEASES

TECHNICAL FIELD

The invention relates to the production method of a product that is developed for treatment of hair loss, alopecia areata (pelade or ringworm), androgenetic alopecia (AGA), hair follicle nourishment, scalp nourishment and scar, scar tissue, eczema, acne treatments, for neurodegenerative, inflammatory diseases and for immune modulation purposes (regulation of the immunological response against inflammation of human tissues and fluids, for regeneration purposes).

In particular, the invention relates to a method for the production of a chemical-free product with amniotic fluid content, which has been standardized by pooling and then freeze-dried and gamma irradiated (pooled/cocktail and gamma irradiated amnion-OTIA 1.0), that has been developed to be used in the treatment of ailments such as hair loss, alopecia areata (pelade), androgenetic alopecia (AGA), hair follicle nutrition, scalp nourishment, scar, scar tissue, eczema and acne.

Known State of the Art

Alopecia, which means hair loss in medical language, is a common problem that occurs as genetic, hormonal, traumatic and iatrogenic forms. Pelade (alopecia areata) is an autoimmune disorder characterized by regional hair loss in which the hair follicle and nails are affected. There are pelade varieties that have different characteristics from each other. Alopecia areata disease is divided into many subtypes. Pelade is the most common of these subtypes. The type of alopecia in which all the hair on the scalp is affected is called "alopecia totalis". When this effect covers the whole body, it is called "alopecia universalis". In some people, sudden excessive thinning and weakening of hair without hair opening is defined as "diffuse alopecia areata". Pelade cases, in which hair losses occur in the form of hair bands on the nape and behind the ears instead of round patches, are called "ofiasis". Androgenic alopecia (AGA) is a disease that occurs with the effect of androgens; it can be seen in both sexes and is characterized by hair loss. In addition to the problem of hair loss that develops with age, it has become a problem in women and especially in men due to stress and diseases.

Alopecia areata is also a very complicated disorder regarding the healing process. In some people, many alopecia areata treatment methods can be tried to determine which application is more effective. Today, especially in dermatology outpatient clinics, there are various treatment options in the treatment of Alopecia Areata such as oral and topical drugs or mesotherapy, surgery. Topical treatment includes corticosteroids, minoxidil and immunotherapy. Contact immunotherapy with diphenylcyclopropenone and karec acid dibutylester is mainly used for limited hair loss. However, these drugs have inadequate treatment methods, cause side effects, and have limited therapeutic uses. At the same time, autologous single follicle and follicular unit transplantation has been a reliable surgical option, but the number of donor follicles also limits this method.

Scars due to alopecia areata and scars in general that occur on the skin independently of alopecia areata are another dermis problem. Numerous methods for the treatment of abnormal scars have been described, but to date, the optimal method of treatment has not been established. In this regard, the ability of the amniotic fluid is that intrauterine interventions heal without leaving scars, so it is likely to play a role in scar/hypertrophic scar treatments. Studies have shown that human amniotic fluid stem cells can accelerate cutaneous wound healing with fewer fibrotic scars along with their effect on fetal wound healing. However, in the method we use, the amniotic fluid is pooled, frozen and gamma-irradiated, making this product more reliable, effective and it has a longer shelf life.

Amniotic fluid is the living environment of the fetus. It appears together with the embryo, protects and feeds the fetus throughout pregnancy; its existence and function end with childbirth. 99% of the amniotic fluid is water, the remaining 1% consists of inorganic salts, organic substances and epithelial cells shed from the fetus. The fact that amniotic fluid is not used immediately after birth increases the importance of sterilization of the preservation of the material. Furthermore, the fact that the biological material is vulnerable to contamination in liquid form makes it difficult to isolate, preserve and for the final product to have a long life. Accordingly, the increase in impurities adversely affects the stability of the product. On the other hand, the supply of amniotic fluid during the birth of cattle in these techniques reduces product safety and the preference of the treatment by the patient.

The following applications have been found on the subject in the literature:

The patent application numbered 2019/14272 relates to the production method for pelade and eczema treatment fluid and products produced by the method, which consists entirely of herbal and natural products. The invention describes the method of combining all herbal and natural products to be used in the cosmetic and treatment industry and the products that will be used in pelade treatment, eczema treatment, scalp treatment, scalp cleaning, hair follicle exposure, pimple and acne treatment on the head, hair follicle nutrition, scalp nutrition and dandruff treatment.

The European patent application numbered EP3145490B1 relates to liposomes containing Di homo gamma linolenic acid (dgla), formulations containing them and their use. The said application describes liposomes formulated for topical and/or oral use, and preferably for topical use, containing active ingredients to be used for the treatment of alopecia, baldness, hair loss, as well as for hair regrowth in postmenopausal women and in general.

In the patent document TR2016/04762 included in the technique, methods and compositions are explained for the reproduction and isolation of a cell population derived from amniotic fluid that can differentiate in the form of ß-cell series and used in the treatment of therapeutic diabetes. The therapeutic use of amniotic components is also present in skin diseases. For example, the patent document CN107217028, mentions that the amniotic membrane can be used in tissue engineering. The document describes a method of healing damaged tissue. In another document numbered WO2010107287, a method for triggering hair growth with the use of mesenchymal stem cells of fetus origin contained in amniotic fluid is described.

In summary, there is no effective treatment for alopecia and scar treatments. In the current literature review, it has been seen that amniotic fluid cells and/or exosomes are used in the treatment of scar, but there is no usage that includes the described method. In addition, the use of amniotic fluid in the clinic for the treatment of neurodegenerative, inflammatory diseases and immune modulation (by changing the behavior of one or more of the human immune cells in vitro or in vivo) is still out of the question. Also, local, intradermal, non-subcutaneous uses of amniotic fluid in accordance with the objectives defined above are not available. In other words, amniotic fluid is still not used in the clinic by intravenous, intramuscular, endobronchial, intrathecal methods or by inhalation.

Therefore, due to the drawbacks described above and the inadequacy of the existing solutions on the subject, it became necessary to make an improvement in the relevant technical field.

Objective of the Invention

The present invention relates to a method for the production of a product which meets the requirements mentioned above, eliminates all disadvantages and brings some additional advantages and is suitable for use in the treatment of hair loss, hair follicle nutrition, scalp nourishment and scar tissue, eczema and acne treatments, as well as neurodegenerative, inflammatory diseases.

The main objective of the invention relates to a method for the production of a product developed for use in hair loss, alopecia areata (pelade), androgenetic alopecia (AGA), hair follicle nourishment, scalp nourishment, scar, wound, eczema and acne treatments, where the natural deviations are minimized with the pooling method and the product is made safe and more reliable by freezing and gamma irradiation.

An objective of the invention is to develop a method that allows the use of amniotic fluid in neurodegenerative, inflammatory diseases and for immune modulation purposes (by changing the behavior of one or more of the human immune cells in vitro or in vivo) through local, intravenous, intramuscular, endobronchial, intrathecal methods and by inhalation.

Another objective of the invention is related to a method for the production of a product that prevents hair loss by triggering cell renewal by means of its amniotic fluid content and revitalizes the hair follicles that have lost their function and ensures re-growth of hair in the areas where hair has been lost.

Another objective of the invention relates to a method to produce a product that provides treatment of scarred tissues in the skin without resection by triggering cell regeneration by means of its amniotic fluid content.

Another objective of the invention relates to a method in which amniotic fluid obtained from the mother's womb is used, with the consent of the mother at the time of caesarean section.

Another objective of the invention relates to a method to produce a product that is stored in solid form, thus whose stability and shelf life are extended.

Another objective of the invention relates to a method in which amniotic fluid is taken from plurality of mothers and pooled together to standardize it by removing individual differences.

In order to achieve the objectives described above, the invention is a method for the production of a product suitable for use in the treatment of hair loss, alopecia areata (pelade or ringworm), androgenetic alopecia, hair follicle nutrition, scalp nourishment, eczema and acne treatment, scarring, wound treatment and by local or subdermal injection and for use in neurodegenerative, inflammatory diseases by total inhalation, intravenous, intramuscular injection and comprises the following process steps;

i. Collecting amniotic fluid from at least three different sources, ii. Centrifuging amniotic fluids for the removal of macroparticles, iii. Staged filtration of centrifuged amniotic fluid, iv. Pooling of amniotic fluids from different sources together v. Freezing of the amniotic fluid at −80° C. to −40° C., and vi. Irradiation in frozen form between 25-35 Kgy It is a product produced by the method, which is the subject of the invention, for achieving the objectives described above, that is dissolved into a solution and that is suitable for inhalation or for local use on the skin and for subcutaneous, intradermal, endobronchial, intravenous, intramuscular injections.

The structural and characteristic features of the invention and all its advantages will be understood more clearly by means of the detailed description. For this reason, evaluation should be made by taking this detailed explanation into consideration.

DETAILED DESCRIPTION OF THE INVENTION

In this detailed description, preferred embodiments of a method for the production of a product, which is the subject of the invention, that is developed for treatment of hair loss, alopecia areata (pelade or ringworm), androgenetic alopecia (AGA), hair follicle nourishment, scalp nourishment and scar, wound, eczema, acne treatments, for neurodegenerative, inflammatory diseases and for immune modulation purposes (regulation of the immunological response against inflammation of human tissues and fluids, for regeneration purposes) only for a better understanding of the subject and in a way that does not cause any limiting effect.

The invention is a method for the production of a product suitable for use in the treatment of hair loss, alopecia areata (pelade or ringworm), androgenetic alopecia, hair follicle nutrition, scalp nourishment, eczema and acne treatment, scarring, wound treatment and by local or subdermal injection and for use in neurodegenerative, inflammatory diseases by total inhalation, intravenous, intramuscular injection and comprises the following process steps;

i. Collecting amniotic fluid from at least three different sources, ii. Centrifuging amniotic fluids for the removal of macroparticles, iii. Staged filtration of centrifuged amniotic fluid, iv. Pooling of amniotic fluids from different sources together v. Freezing of the amniotic fluid at −80° C. to −40° C., and vi. Irradiation in frozen form between 25-35 Kgy.

In the preferred embodiment of the invention, the amniotic fluids mentioned in the process step (i) are supplied from the abdomen of mothers who have undergone a healthy birth process with their consent at the time of cesarean section or normal delivery. In this respect, it is also possible to recover a biological material that will be disposed of as medical waste without being utilized under normal conditions. In the most preferred embodiment of the invention, amniotic fluid is collected from at least 3, ideally 7 to 10 different mothers in step (i). Here, in the process step (i), simultaneous collection of amniotic fluids within maximum 24 hours is an extremely important element in ensuring that the standards of a pooled product are maintained. The objective here is to prevent the deviations of more than one amniotic fluid that will be pooled due to time difference. For example, if two amniotic fluids are collected on the first day, then one or two more collected samples will have to be pooled together after two days, the samples on the first day will have to be frozen and stored, on the day the second sample arrives, it will have to be defrosted to be pooled it, and then frozen again. Thus, the sample collected on the first day will have to go through an extra freezing-defrosting cycle and this will adversely affect the final sample quality and there will be differences from one product to another. That is why collecting from multiple sources simultaneously is so important. And it is a method specific to the subject of our application.

In the preferred embodiment of the invention, differences in genomics/biochemical/biomix of biological materials from different mothers are standardized in a way that minimizes the difference from product to product by means of the pooling process mentioned in process step (i).

In the preferred embodiment of the invention, the centrifuge mentioned in process step (ii) is carried out for a minimum of 800 gr for at least 10 minutes to remove macro particles from amniotic fluids.

According to the preferred embodiment of the invention, the filtration process mentioned in process step (iii) involves passing of the amniotic fluid through the filters in at least two stages. According to the preferred embodiment, the amniotic fluid is first passed through the filter with a mesh size of 0.3-1 microns, and then through the filter with a mesh size of 0.01-0.3 microns. These specifically selected mesh ranges guarantee complete purification of the amniotic fluid from impurities in terms of cell and macro vesicles and bacterial content. In the most preferred embodiment, the amniotic fluid is first passed through a 0.44 micron filter and then through a 0.22 micron filter.

In the preferred embodiment of the invention, the freezing process mentioned in process step (v) involves freezing the amniotic fluid, which is filtered and purified from macro impurities, at −80° C. to −40° C. While this process ensures the stabilization of the product, it will also protect the amniotic material from the heat shock that will be caused by gamma radiation before irradiation. This process is preferably done by means of deep freezers within maximum 24 hours following the collection of the product (i).

According to the preferred embodiment of the invention, the amniotic material that has been frozen into solid form is sterilized by irradiation with 25-35 Kgy gamma radiation in the frozen state in the process step (vi) and stabilized by prosthesis inactivation by irradiation. Irradiation of amniotic material, especially in frozen form, provides an additional benefit by protecting it from thermal shock caused by radiation. For this reason, irradiation by freezing is extremely important. While irradiation with gamma radiation makes the product safe for bacterial, viral and prion contamination, the inhibition of protease activity caused by gamma radiation also increases the sterility of the product.

In order to provide the necessary safety data for the local, intradermal, non-subcutaneous use of the product produced by the method of the invention, necessary analyzes such as microbiological analysis, endotoxin surface measurement, macro particle control, product protein electrolyte determination, stoking profile analyzes and osmolality determination, etc. are carried out with the appropriate method.

It has been observed that the product produced by the method of the invention prevents hair loss by triggering cell renewal and revitalizes the hair follicles that have lost their function and provides hair growth again in the areas of hair loss. Its therapeutic effect has been tested not only on the scalp, but also on scar tissue with or without hair, and it has been shown that it provides treatment of scarred tissues in the skin without resection.

After the frozen and irradiated sterile amniotic fluid produced by the method of invention is dissolved into a solution, it can be applied to the problem area by injector and similar methods by local, intradermal and subcutaneous, intravenous, intramuscular, endobronchial, intrathecal methods or by inhalation according to preference. Therefore, apart from alopecia and scar treatment, it can be used in neurodegenerative, inflammatory diseases and for immune modulation (changing the behavior of one or more of the human immune cells in vitro or in vivo) purposes.

The invention claimed is:

1. A process for producing a product for use by local or subdermal or intravenous or intramuscular injection, the product for use in a treatment of at least one of for hair loss, for alopecia areata (ringworm), for androgenetic alopecia, for hair follicle nutrition, for scalp nourishment, for eczema, for acne, for scarring, for wound treatment, for neurodegenerative diseases, for inflammatory diseases, the process comprising:
   collecting an amniotic fluid from at least three different sources;
   centrifuging the collected amniotic fluid so as to remove macroparticles therefrom;
   staged filtering of the centrifuged amniotic fluid;
   pooling together the filtered centrifuged amniotic fluid from the at least three different sources;
   freezing the pooled amniotic fluid at a temperature of between −80° C. and −40° C.; and
   irradiating the frozen pooled amniotic fluid at a kilogray level of between 25 and 35.

2. The process of claim 1, wherein the at least three amniotic fluids are obtained from respective abdomens of mothers at a time of a caesarean section of the mothers.

3. The process of claim 1, wherein the at least three amniotic fluids are collected from at least three mothers.

4. The process of claim 1, wherein the step of staged filtering comprising:
   passing the centrifuged amniotic fluid through at least two filter stages.

5. The process of claim 1, wherein the step of staged filtering comprises:
   passing the centrifuged amniotic fluid through a first filter that has a mesh size of between 0.3 microns and 1 micron; and
   subsequently passing the centrifuged amniotic fluid through a second filter having a mesh size of between 0.1 microns and 0.3 microns.

6. The process of claim 1, wherein the step of pooling combines ten amniotic fluids.

7. The process of claim 1, wherein the step of freezing is carried out for a period of time less than twenty-four hours following the step of collecting.

* * * * *